(12) United States Patent
Matsubara

(10) Patent No.: US 9,643,104 B2
(45) Date of Patent: May 9, 2017

(54) LIQUID CHROMATOGRAPHY DEVICE, LIQUID CHROMATOGRAPHY ANALYSIS PROCESS, AND NON-TRANSITORY COMPUTER-READABLE MEDIUM FOR LIQUID CHROMOTOGRAPHY ANALYSIS

(71) Applicant: ARKRAY, Inc., Kyoto-shi (JP)

(72) Inventor: Takeshi Matsubara, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 182 days.

(21) Appl. No.: 14/453,400

(22) Filed: Aug. 6, 2014

(65) Prior Publication Data

US 2015/0040648 A1 Feb. 12, 2015

(30) Foreign Application Priority Data

Aug. 7, 2013 (JP) ................................. 2013-164251
Aug. 8, 2013 (JP) ................................. 2013-165461
Aug. 1, 2014 (JP) ................................. 2014-157936

(51) Int. Cl.
*B01D 15/42* (2006.01)
*B01D 15/26* (2006.01)
*G01N 30/24* (2006.01)
*G01N 30/88* (2006.01)
(Continued)

(52) U.S. Cl.
CPC ......... *B01D 15/424* (2013.01); *B01D 15/166* (2013.01); *B01D 15/265* (2013.01);
(Continued)

(58) Field of Classification Search
CPC ............... G01N 30/02; G01N 2030/27; G01N 2030/25; G01N 30/38; G01N 2030/382; G01N 2030/385; B01D 15/424
See application file for complete search history.

(56) References Cited

U.S. PATENT DOCUMENTS 4,112,743 A 9/1978 Mowery, Jr.
5,607,581 A 3/1997 Gerner et al.
(Continued)

FOREIGN PATENT DOCUMENTS

| CN | 102171562 | 8/2011 |
| EP | 1536228 A1 | 6/2005 |
| JP | 2007-212277 A | 8/2007 |
| JP | 2009-139376 A | 6/2009 |
| WO | WO-2010/041637 A1 | 4/2010 |

OTHER PUBLICATIONS

Extended European Search Report dated Dec. 10, 2014 issued in the corresponding European patent application No. 14180015.1.
(Continued)

*Primary Examiner* — Erika J Villaluna
(74) *Attorney, Agent, or Firm* — Fox Rothschild LLP

(57) ABSTRACT

A liquid chromatography device includes an adsorption portion that adsorbs one or more analysis components in a specimen, an analysis device that analyzes an analysis component eluted by an eluent, a main feeding device that feeds a first eluent to the adsorption portion, the first eluent eluting an analysis component, a feeding channel in fluid communication with the main feeding device and the adsorption portion, a first retention channel that retains a second eluent, the second eluent differing from the first eluent, an auxiliary feeding device that feeds the second eluent to the first retention channel, and a first switching device that switches the feeding channel to either a first channel or a second channel, the first channel allowing the first eluent to flow from the main feeding device to the adsorption portion, and the second channel allowing the second eluent to flow from the first retention channel to the adsorption portion.

14 Claims, 8 Drawing Sheets

(51) Int. Cl.
*B01D 15/16* (2006.01)
*G01N 30/34* (2006.01)
*G01N 30/02* (2006.01)
*B01D 19/00* (2006.01)
*G01N 30/20* (2006.01)

(52) U.S. Cl.
CPC ............ *G01N 30/24* (2013.01); *G01N 30/34* (2013.01); *G01N 30/88* (2013.01); *B01D 19/00* (2013.01); *G01N 2030/027* (2013.01); *G01N 2030/201* (2013.01); *G01N 2030/202* (2013.01); *G01N 2030/207* (2013.01); *G01N 2030/8804* (2013.01); *G01N 2030/8822* (2013.01)

(56) References Cited

U.S. PATENT DOCUMENTS

2010/0288024 A1* 11/2010 Sugiyama .......... B01D 19/0036
  73/61.52
2011/0186511 A1* 8/2011 Sakai .................... G01N 30/24
  210/635
2013/0008523 A1 1/2013 Witt et al.

OTHER PUBLICATIONS

Dthce Action issued in the corresponding Chinese Patent Application No. 201410384026.0 dated Jan. 17, 2017.

* cited by examiner

LIQUID CHROMATOGRAPHY DEVICE, LIQUID CHROMATOGRAPHY ANALYSIS PROCESS, AND NON-TRANSITORY COMPUTER-READABLE MEDIUM FOR LIQUID CHROMOTOGRAPHY ANALYSIS

CROSS-REFERENCE TO RELATED APPLICATION

This application is based upon and claims the benefit of priority of the prior Japanese Patent Application No. 2014-157936, filed on Aug. 1, 2014, Japanese Patent Application No. 2013-164251, filed on Aug. 7, 2013, and Japanese Patent Application No. 2013-165461, filed on Aug. 8, 2013, the entire contents of which are incorporated herein by reference.

FIELD

The present invention relates to a liquid chromatography device, a liquid chromatography analysis process, and a non-transitory computer-readable medium.

BACKGROUND

Analysis devices that analyze components in samples include a liquid chromatography device (for example, see Japanese Patent Application Laid-Open (JP-A) No. 2007-212277) in which components in a sample are adsorbed to an adsorption portion such as a column or the like, an eluent is supplied to the adsorption portion and a particular component is separated, after which the component in the eluent is analyzed by a measurement device.

Another liquid chromatography device (for example, see the Specification of WO 2010/041637) is equipped with a constant rate pump that feeds a first eluent and an introduction channel that introduces another eluent. A first switching valve is provided that is capable of introducing the first eluent into the introduction channel. The constant rate pump feeds the two or more kinds of eluent in an unmixed state to an adsorption portion via the first switching valve. A further liquid chromatography device (for example, see JP-A No. 2009-139376) employs a high-pressure injection valve for switching required liquid flows, thus enabling very large pressure differences.

SUMMARY

A liquid chromatography device according to a first aspect includes: an adsorption portion that adsorbs one or more analysis components in a specimen; an analysis device that analyzes an analysis component eluted by an eluent; a main feeding device that feeds a first eluent to the adsorption portion, the first eluent eluting an analysis component; a feeding channel in fluid communication with the main feeding device and the adsorption portion; a first retention channel that retains a second eluent, the second eluent differing from the first eluent; an auxiliary feeding device that feeds the second eluent to the first retention channel; and a first switching device that switches the feeding channel to either a first channel or a second channel, the first channel allowing the first eluent to flow from the main feeding device to the adsorption portion, and the second channel allowing the second eluent to flow from the first retention channel to the adsorption portion.

In the liquid chromatography device according to the first aspect, the first eluent is fed to the adsorption portion via the feeding channel by the main feeding device. Analysis components in the specimen are adsorbed at the adsorption portion. The analysis component that is eluted by the first eluent is analyzed by the analysis device.

The second eluent is fed to the first retention channel by the auxiliary feeding device. The feeding channel can be switched from the first channel to the second channel by the first switching device. Hence, the second eluent retained in the first retention channel can be pushed out to the adsorption portion by the first eluent being introduced into the first retention channel. The analysis component that is eluted by the second eluent is analyzed by the analysis device. Thus, with a simple structure, plural liquids divided between a high-pressure channel and a low-pressure channel may be processed in parallel quickly and easily.

The feeding channel and the first retention channel may be formed as channels that are narrow enough to prevent mixing of the eluents with one another. Thus, the second eluent that is pushed out from the first retention channel can be fed to the adsorption portion in an unmixed state with the first eluent.

In a second aspect, in the liquid chromatography device according to the first aspect, further included are: a second retention channel that retains a third eluent, the third eluent differing from the first and second eluents; an auxiliary feeding device that feeds the third eluent to the second retention channel; and a second switching device that switches the feeding channel to either the first channel or a third channel, the third channel allowing the third eluent to flow from the second retention channel to the adsorption portion.

In the liquid chromatography device according to the second aspect, the third eluent is fed to the second retention channel by the auxiliary feeding device. The feeding channel can be switched from the first channel to the third channel by the second switching device. Thus, the third eluent retained in the second retention channel can be pushed out to the adsorption portion by the first eluent being introduced into the second retention channel. An analysis component that is eluted by the third eluent is analyzed by the analysis device.

The feeding channel and the second retention channel may be formed as channels that are narrow enough to prevent mixing of the eluents with one another. Thus, the third eluent that is pushed out from the second retention channel can be fed to the adsorption portion in an unmixed state with the first eluent.

In a third aspect, in the liquid chromatography device according to the second aspect, further included are: a specimen retention channel that retains the specimen; an auxiliary feeding device that feeds the specimen to the specimen retention channel; and a third switching device that switches the feeding channel to either the first channel or a fourth channel, the fourth channel allowing the specimen to flow from the specimen retention channel to the adsorption portion.

In the liquid chromatography device according to the third aspect, the specimen is fed to the specimen retention channel by the auxiliary feeding device. The feeding channel can be switched from the first channel to the fourth channel by the third switching device. Thus, the specimen retained in the specimen retention channel can be pushed out to the adsorption portion by the first eluent being introduced into the specimen retention channel.

The feeding channel and the specimen retention channel may be formed as channels that are narrow enough to prevent mixing of the liquids with one another. Thus, the specimen that is pushed out from the specimen retention channel can be fed to the adsorption portion in an unmixed state with the first eluent.

In a fourth aspect, in the liquid chromatography device according to the second aspect, the auxiliary feeding device that feeds the second eluent and the auxiliary feeding device that feeds the third eluent are configured the same device.

In the liquid chromatography device according to the fourth aspect, the auxiliary feeding device that feeds the second eluent and the auxiliary feeding device that feeds the third eluent are a shared device. Thus, the number of device components may be reduced and operations may be conducted efficiently.

In a fifth aspect, in the liquid chromatography device according to the third aspect, the auxiliary feeding device that feeds the specimen is the same device as at least one of the auxiliary feeding device that feeds the second eluent or the auxiliary feeding device that feeds the third eluent.

In the liquid chromatography device according to the fifth aspect, the auxiliary feeding device that feeds the specimen is a shared device with at least one of the auxiliary feeding device that feeds the second eluent or the auxiliary feeding device that feeds the third eluent. Thus, the number of device components may be reduced and operations may be conducted efficiently.

In a sixth aspect, in the liquid chromatography device according to any one of the first to fifth aspects, the first switching device enables parallel operation of a bubble elimination process and another process, the processes using the main feeding device and the auxiliary feeding device.

In the liquid chromatography device according to the sixth aspect, by switching of the first switching device, bubble elimination by a bubble elimination device that is the main feeding device and another process by the auxiliary feeding device may be operated in parallel.

In a seventh aspect, in the liquid chromatography device according to the first aspect, further included is a liquid dilution device that dilutes the specimen containing the one or more analysis components, wherein the adsorption portion adsorbs the one or more analysis components in the specimen that has been diluted by the liquid dilution device.

In the liquid chromatography device according to the seventh aspect, the analysis components of the specimen may be adsorbed at the adsorption portion after the specimen has been diluted by the liquid dilution device.

A liquid chromatography analysis process according to an eighth aspect includes: an elution step of, at a main feeding device, feeding a first eluent that elutes an analysis component through a feeding channel to an adsorption portion that has adsorbed one or more analysis components in a specimen and eluting the analysis component; an analysis step of, at an analysis device, analyzing the analysis component eluted in the elution step; a first retention step of, at an auxiliary feeding device, feeding a second eluent to and retaining the second eluent at a first retention channel, the second eluent differing from the first eluent; and a first switching step of switching the feeding channel to either a first channel or a second channel, the first channel allowing the first eluent to flow from the main feeding device to the adsorption portion, and the second channel allowing the first eluent to flow through the first retention channel at which the second eluent has been retained to the adsorption portion.

In the liquid chromatography analysis process according to the eighth aspect, in the elution step, the first eluent is fed through the feeding channel to the adsorption portion at which the analysis components in the specimen are adsorbed, and the first eluent elutes an analysis component.

In the analysis step, the analysis component eluted by the first eluent is analyzed by the analysis device. In the first retention step, the second eluent is fed to and retained in the first retention channel. In the first switching step, the feeding channel is switched from the first channel to the second channel, and hence the second eluent that has been retained in the first retention channel is pushed out to the adsorption portion by the first eluent being introduced into the first retention channel. An analysis component elated by the second eluent is analyzed by the analysis device. Thus, with a simple structure, plural liquids divided between a high-pressure channel and a low-pressure channel may be processed in parallel quickly and easily.

In a ninth aspect, in the liquid chromatography analysis process according to the eighth aspect, further included is a step of causing the main feeding device to function as a bubble elimination device.

Bubbles in the eluent may be reduced by this step.

In a tenth aspect, in the liquid chromatography analysis process according to the eighth aspect, further included are a second retention step of, at an auxiliary feeding device, feeding a third eluent to and retaining the third eluent at a second retention channel, the third eluent differing from the first and second eluents; and a second switching step of switching the feeding channel to either the first channel or a third channel, the third channel allowing the first eluent to flow through the second retention channel at which the third eluent has been retained by the second retention step to the adsorption portion.

In the liquid chromatography analysis process according to the tenth aspect, in the second retention step, the third eluent, which differs from the first and second eluents, is fed to and retained in the second retention channel. In the second switching step, the feeding channel is switched from the first channel to the third channel. Hence, the third eluent that has been retained in the second retention channel is pushed out to the adsorption portion by the first eluent being introduced into the second retention channel. An analysis component that is eluted by the third eluent is analyzed by the analysis device.

In an eleventh aspect, in the liquid chromatography analysis process according to the tenth aspect, further included is a specimen retention step of, at an auxiliary feeding device, feeding the specimen to and retaining the specimen at a specimen retention channel, wherein the elution step includes a specimen introduction step of switching the feeding channel from the first channel to a fourth channel, the fourth channel allowing the first eluent to flow through the specimen retention channel at which the specimen has been retained by the specimen retention step to the adsorption portion.

In the liquid chromatography analysis process according to the eleventh aspect, in the specimen retention step, the specimen is fed to and retained in the specimen retention channel. In the specimen introduction step, the feeding channel is switched from the first channel to the fourth channel. Thus, the specimen retained in the specimen retention channel can be pushed out to the adsorption portion by the first eluent being introduced into the specimen retention channel.

A liquid chromatography analysis program according to a twelfth aspect causes a liquid chromatography device that includes: an adsorption portion that adsorbs one or more analysis components in a specimen; an analysis device that analyzes an analysis component eluted by an eluent; a main feeding device that feeds a first eluent to the adsorption portion, the first eluent eluting an analysis component; a feeding channel in fluid communication with the main feeding device and the adsorption portion; a first retention channel that retains a second eluent, the second eluent differing from the first eluent; an auxiliary feeding device that feeds the second eluent to the first retention channel; a first switching device that switches the feeding channel to either a first channel or a second channel, the first channel allowing the first eluent to flow from the main feeding device to the adsorption portion, and the second channel allowing the second eluent to flow from the first retention channel to the adsorption portion; and a computer that controls the main feeding device, the analysis device, the auxiliary feeding device and the first switching device, to execute a process including: an elution step of, at the main feeding device, feeding the first eluent to the adsorption portion and eluting the analysis component; an analysis step of, at the analysis device, analyzing the analysis component eluted in the elution step; a first retention step of, at the auxiliary feeding device, feeding the second eluent to and retaining the second eluent at the first retention channel; and a first switching step of, with the first switching device, switching the feeding channel from the first channel to the second channel.

In the liquid chromatography analysis program according to the twelfth aspect, in the elution step, the first eluent is fed by the main feeding device through the feeding channel to the adsorption portion at which the analysis components in the specimen are adsorbed, and an analysis component is eluted. In the analysis step, the analysis component eluted by the first eluent is analyzed by the analysis device. In the first retention step, the second eluent is fed to and retained in the first retention channel by the auxiliary feeding device. In the first switching step, the feeding channel is switched from the first channel to the second channel by the first switching device. Hence, the second eluent that has been retained in the first retention channel is pushed out to the adsorption portion by the first eluent being introduced into the first retention channel. An analysis component eluted by the second eluent is analyzed by the analysis device. Thus, with a simple structure, plural liquids divided between a high-pressure channel and a low-pressure channel may be processed in parallel quickly and easily.

DESCRIPTION OF EMBODIMENTS

—First Exemplary Embodiment—
Overall Structure

An exemplary embodiment of the liquid chromatography device according to the present invention is described below in accordance with FIG. 1 to FIG. 8. A liquid chromatography device 1 according to the present exemplary embodiment is a device that carries out fully automatic high-performance liquid chromatography (HPLC). HPLC measures, for example, glycohemoglobin concentrations in blood samples using liquids (eluents) that elute analysis components.

Figure 1:
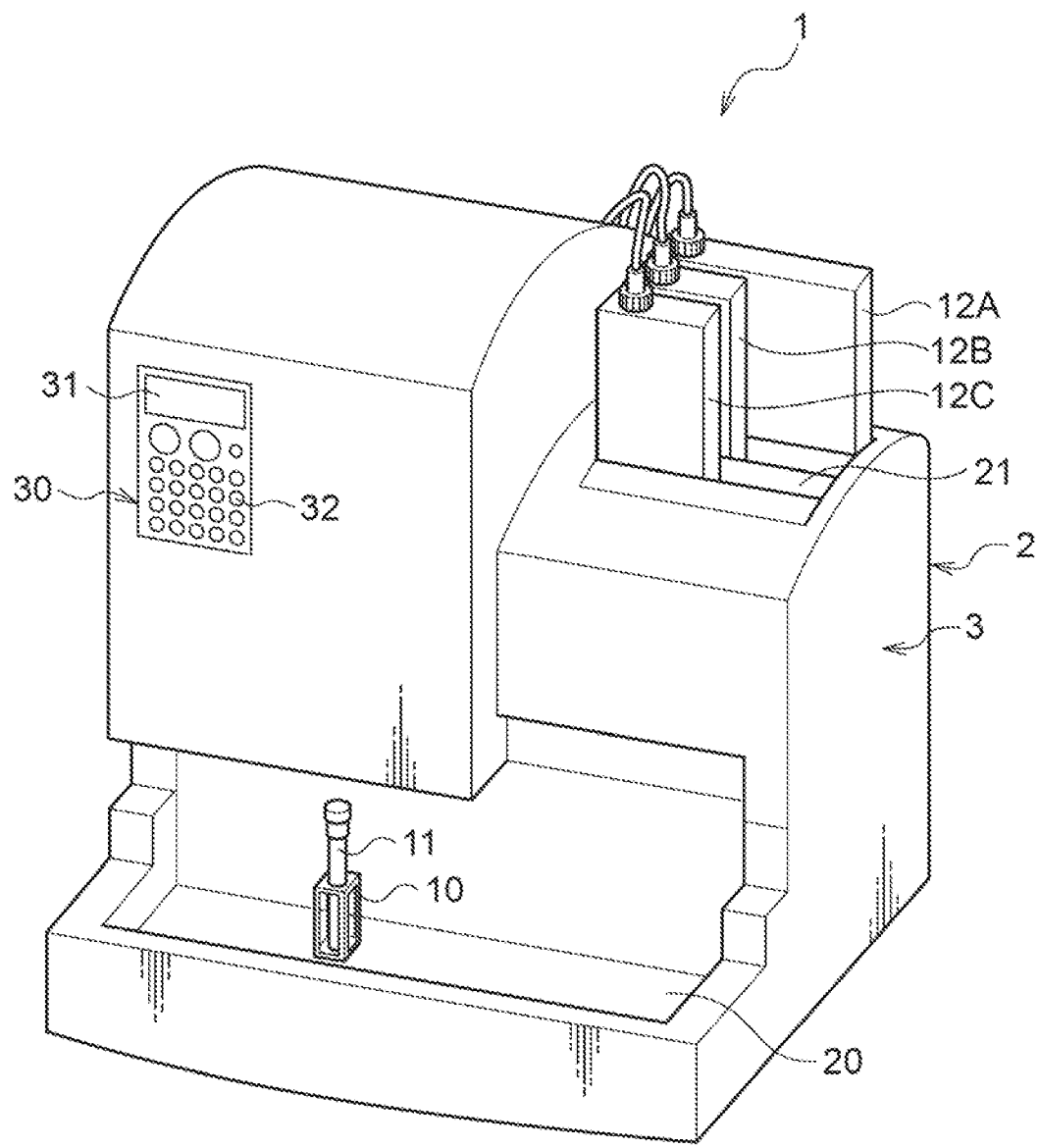
FIG. 1 is a perspective view showing the exterior of a liquid chromatography device in accordance with an exemplary embodiment.

As shown in FIG. 1, the liquid chromatography device 1 according to the present exemplary embodiment includes a device main body 2. The device main body 2 is equipped with a table 20 and a holder section 21.

A blood collection tube 11 retained in a rack 10 is placed on the table 20. A plural number of eluent packs 12 (in the present exemplary embodiment, three eluent packs 12A, 12B and 12C) are placed in the holder section 21. Specifically, the eluent pack 12A accommodates an eluent A that serves as a first eluent, the eluent pack 12B accommodates an eluent B that serves as a second eluent, and the eluent pack 12C accommodates an eluent C that serves as a third eluent.

The eluents A, B and C accommodated in the eluent packs 12A, 12B and 12C have respectively different pH values and salt concentrations and the like, and are for eluting respective analysis components that have adsorbed to a packing material of a column 60, which is described below. Beside the eluent packs 12, a washing fluid bottle 12D that accommodates a dilution and washing fluid is placed in the holder section 21.

The device main body 2 of the liquid chromatography device 1 includes a casing 3. A control panel 30 and a display panel 31 are provided at a front face of the casing 3. The control panel 30 includes plural control buttons 32.

The present exemplary embodiment provides a structure that analyzes a blood sample in a single blood collection tube 11 with a single cycle of measurement, but this is not limiting. A rack that holds a plural number of the blood collection tube 11 may be used, and plural analyses of the blood samples in the blood collection tubes 11 may be successively carried out.

Figure 2:
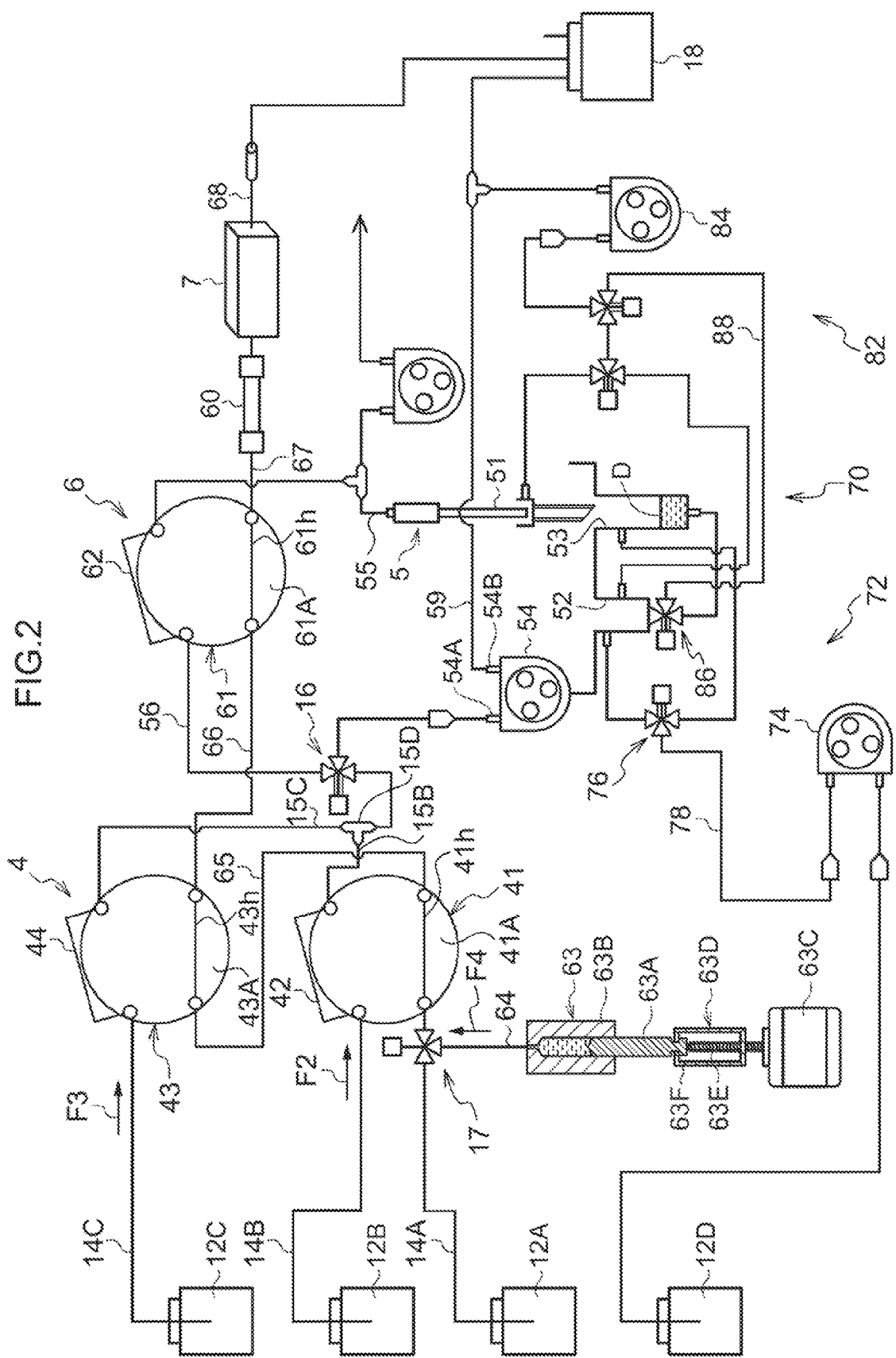
FIG. 2 is a diagram showing internal structures of the liquid chromatography device in accordance with the exemplary embodiment.

An eluent switching unit 4, a specimen preparation unit 5, a separation and adsorption unit 6 and a photometry unit 7, which are shown in FIG. 2, are housed inside the casing 3. The specimen preparation unit 5 draws a blood sample 13 from the blood collection tube 11 (see FIG. 1) and prepares the blood sample 13. The separation and adsorption unit 6 adsorbs and elutes analysis components in the specimen (blood sample) prepared by the specimen preparation unit 5. The photometry unit 7 is an analysis device that performs optical analyses of the analysis components eluted in the separation and adsorption unit 6. The eluent switching unit 4 supplies eluent B and eluent C to the separation and adsorption unit 6.

As is described below, the specimen preparation unit 5 also functions as a liquid dilution device 70.

The specimen preparation unit 5 is equipped with a sample suction nozzle 51, which sucks the blood sample 13 from inside the blood collection tube 11, and a dilution tank 52, which prepares the specimen. The blood sample 13 in the blood collection tube 11 is sucked up by the sample suction nozzle 5 and transferred to the dilution tank 52. The blood sample 13 that has been diluted in the dilution tank 52 is sucked up by the sample suction nozzle 51 at a suitable timing and is fed from the specimen preparation unit 5 to the separation and adsorption unit 6 by driving of a tube pump 54, as is described below.

The separation and adsorption unit 6 is equipped with the column 60, a main pump 63, a feeding channel, and a specimen valve 61. The column 60 is an example of the adsorption portion. The column 60 adsorbs analysis components such as glycohemoglobin and the like from the specimen prepared at the specimen preparation unit 5. The main pump 63 (shown in FIG. 2 at a position that is distant from the reference symbol "6") is an example of the main feeding device. The main pump 63 feeds eluent A toward the column 60. The feeding channel is in fluid communication with the main pump 63 and the column 60, as is described below. The specimen valve 61 is an example of the third switching device. The specimen valve 61 lets the specimen (the blood sample) flow into the feeding channel.

The feeding channel of the present exemplary embodiment is structured by pipelines 64, 65, 66 and 67.

The pipeline 64 (shown in FIG. 2 at a position that is distant from the reference symbol "6") is in fluid communication with the main pump 63 and a first switching valve 41. The first switching valve 41 is an example of the first switching device.

The pipeline 65 (shown in FIG. 2 at a position that is distant from the reference symbol "6") is in fluid communication with the first switching valve 41 and a second switching valve 43. The second switching valve 43 is an example of the second switching device.

The pipeline 66 is in fluid communication with the second switching valve 43 and the specimen valve 61.

The pipeline 67 is in fluid communication with the specimen valve 61 and the column 60.

One end of a pipeline 68 is connected to an outlet side of the column 60. The other end of the pipeline 68 is connected to a waste liquid tank 18. The photometry unit 7 is provided on the pipeline 68.

The main pump 63 is a plunger pump that includes a cylinder 63B (a cylinder unit) a plunger 63A (a rod), a ball screw 63D, and a stepper motor 63C.

The ball screw 63D includes a screw shaft 63E and a nut 63F. The nut 63F is screwed onto the screw shaft 63E, and is fixed to an end of the plunger 63A. When the screw shaft 63E is rotated by the stepper motor 63C, the plunger 63A is reciprocatingly moved by the ball screw 63D. As a result, a distal end of the plunger 63A moves reciprocatingly inside the cylinder 63B.

Thus, when the screw shaft 63E is turned in, for example, a clockwise direction by the stepper motor 63C, the nut 63F moves in a direction away from the stepper motor 63C, and the plunger 63A is pushed toward the cylinder 63B by this movement of the nut 63F. Conversely, when the ball screw 63D is turned in the counterclockwise direction, the nut 63F moves in the direction towards the stepper motor 63C, and the plunger 63A is withdrawn from the cylinder 63B by this movement of the nut 63F.

In the present exemplary embodiment, the main pump 63 has a capacity adequate for an amount of eluent A that is sufficient for a single cycle of analysis operations of one specimen to be drawn into the cylinder 63B by a single pulling operation of the plunger 63A and fed out by a single pushing operation.

A single cycle of processing includes, for example, a measurement start process (equilibration of the column 60), fractionation of the specimen (elution of analysis components adsorbed at the column 60 by the eluents), measurement processing, washing of the column 60, and a post-measurement process (equilibration of the column 60 after washing). The cycle of processing may also include processes other than these, whereas processes among these that are not necessary may be omitted.

With a view to preventing pulsing of the main pump 63 from affecting measurement accuracy and assuring a required accuracy without using a damper, an amount of eluent A that is fed by the main pump 63 may be at least a quantity that is sufficient for fractionation of a single specimen and measurement processing of the specimen. The amount may also be an amount in which a quantity required for one or more of the measurement start process, washing of the column 60 and the post-measurement process is added to the quantity sufficient for the fractionation and measurement processing of the specimen.

A feeding pressure from the main pump 63 during one stroke of eluent A is preferably 1 MPa, may be from 0.15 MPa to 7.5 MPa, may further be from 0.2 MPa to 5 MPa, and more preferably may yet further be from 0.5 MPa to 3 MPa.

A feeding amount of eluent A by the main pump 63 during one stroke may differ between a case of successive measurements of plural specimens and a case of a single measurement of a single specimen. That is, for successive measurements, the main pump 63 may be operated so as to retain rather than feed the last few tenths of the eluent amount for one stroke in the single measurement case, and transfer the retained eluent to the pulling operation for the next measurement. In the present exemplary embodiment, the feeding amount of eluent A by the main pump 63 for one cycle of measurement is preferably from 0.5 mL to 10 mL, is more preferably from 1 mL to 8 mL, and is even more preferably from 1 mL to 6 mL.

In the present exemplary embodiment, as a measurement duration required for one sequence of processing—equilibration of the column, specimen fractionation, measurement processing, column washing and post-measurement processing—up to the completion of data output, for example, a measurement duration from 38 seconds to 10 minutes may be realized. Further, a measurement duration from 38 seconds to 7 minutes may be realized, and still further, a measurement duration from 38 seconds to 6 minutes may be realized.

The specimen valve 61 includes a valve body 61A. The valve body 61A includes a short channel 61*h* and a specimen retention channel 62. A channel length of the specimen retention channel 62 is longer than the channel length of the short channel 61*h*.

Figure 3:
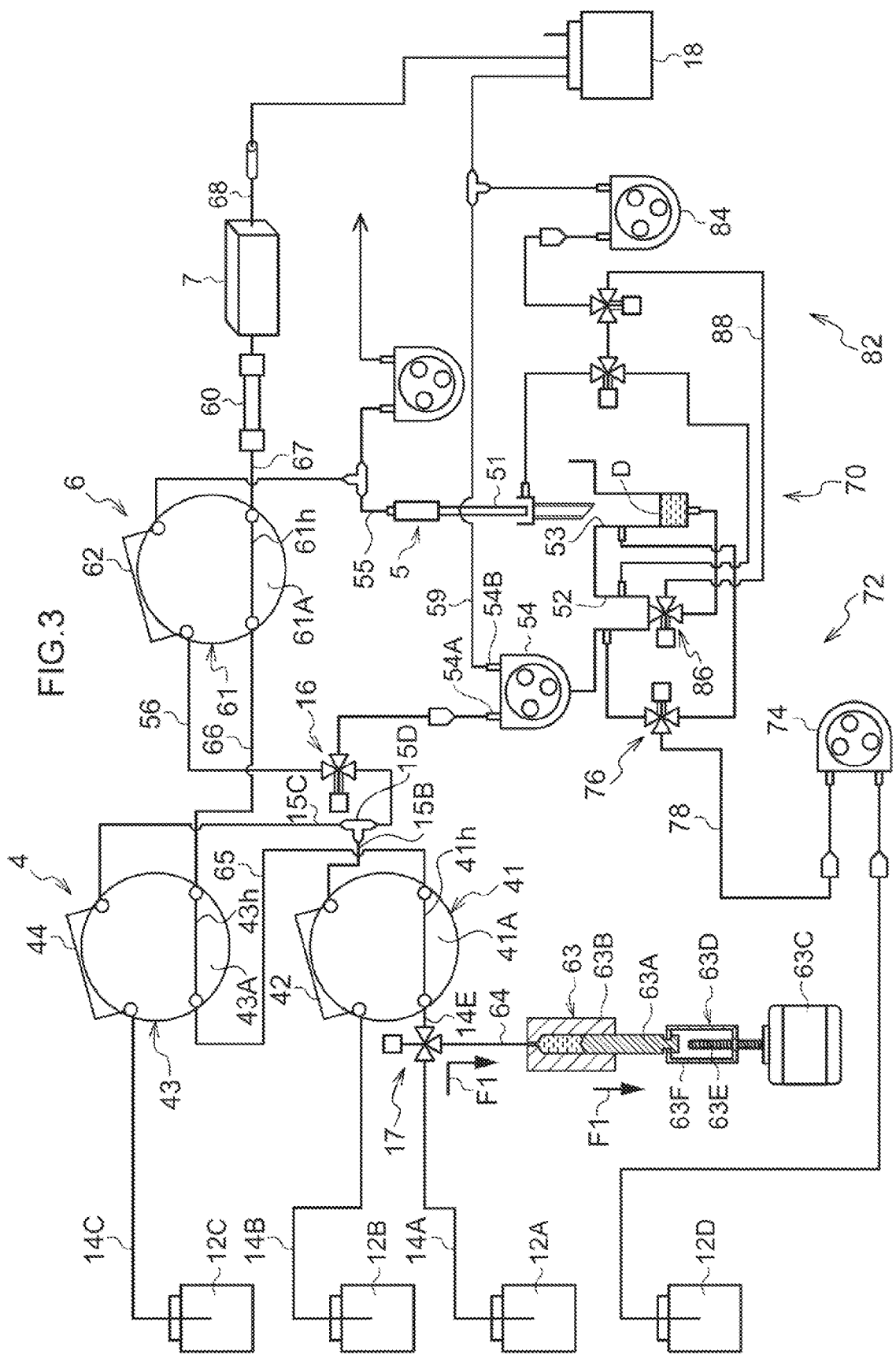
FIG. 3 is a diagram showing a state of the liquid chromatography device in accordance with the exemplary embodiment in which a first switching valve is switched such that an eluent A flows into a main pump.
Figure 4:
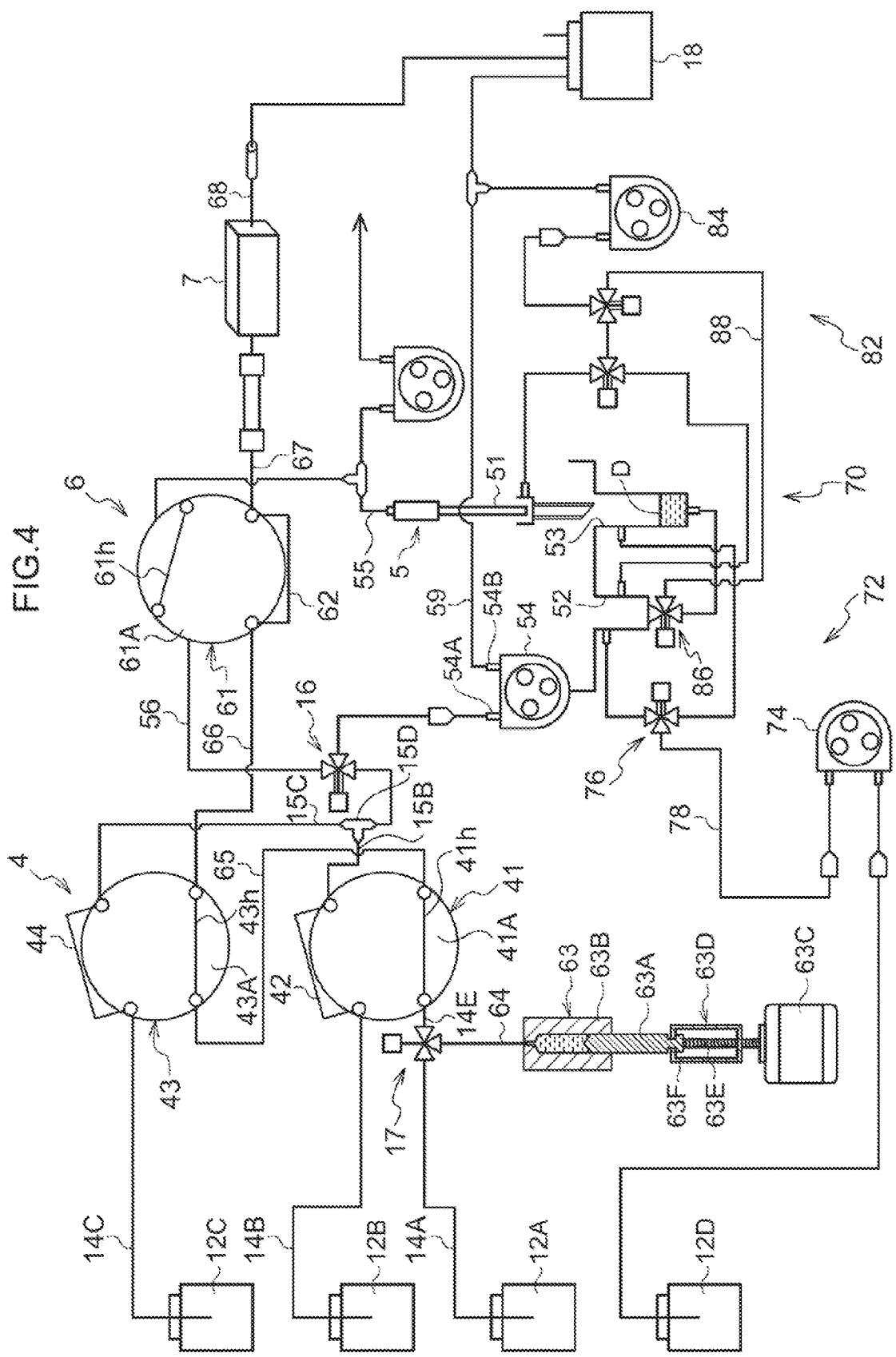
FIG. 4 is a diagram showing a state of the liquid chromatography device in accordance with the exemplary embodiment in which a specimen valve is switched such that a specimen in a specimen retention channel is fed to a column.
Figure 5:
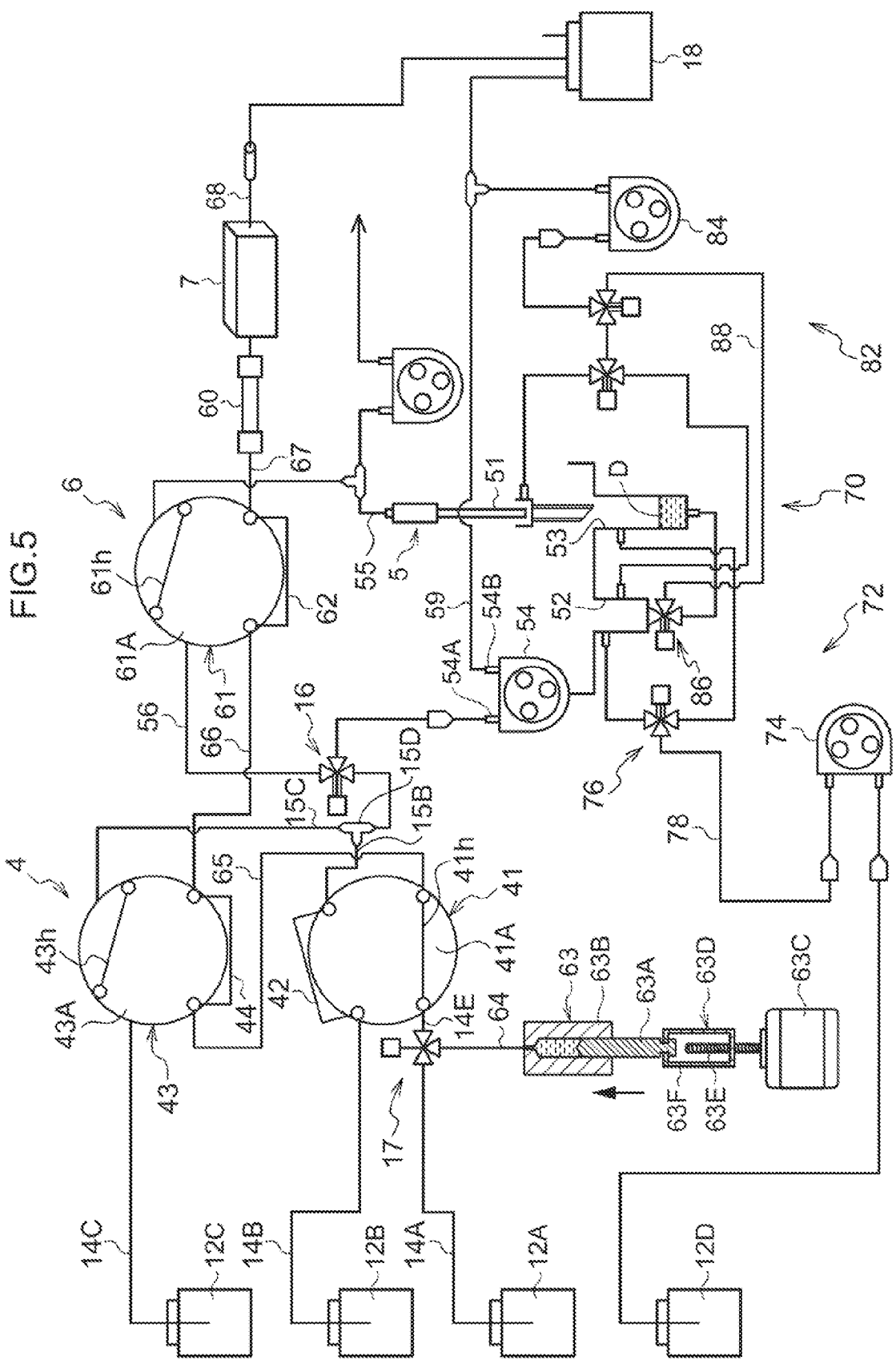
FIG. 5 is a diagram showing a state of the liquid chromatography device in accordance with the exemplary embodiment in which a second switching valve is switched such that an eluent C in an eluent retention channel is fed to the column.
Figure 6:
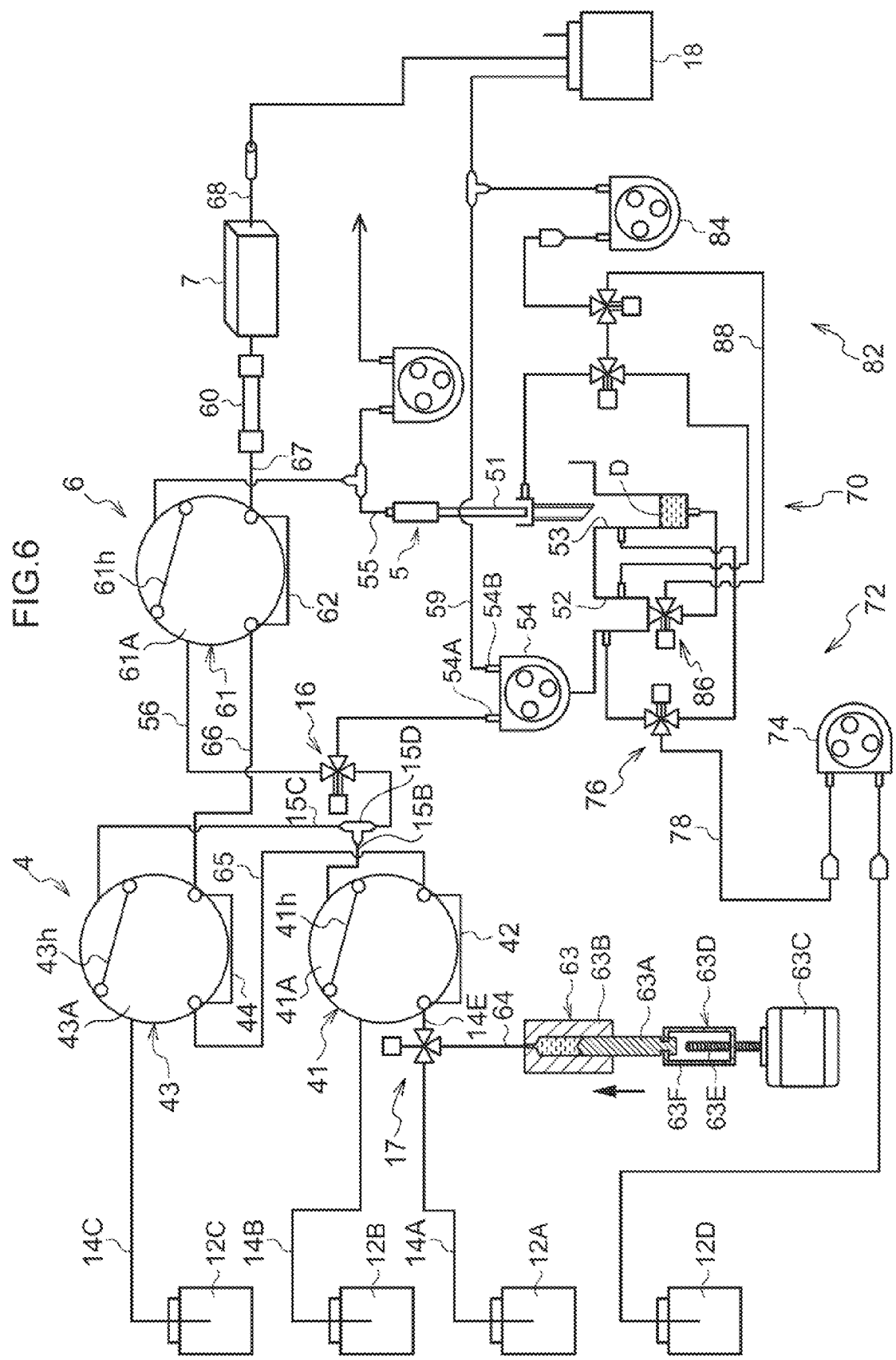
FIG. 6 is a diagram showing a state of the liquid chromatography device in accordance with the exemplary embodiment in which the first switching valve is switched such that an eluent B in an eluent retention channel is fed to the column.

By turning, the valve body 61A can assume two states: state A shown in FIG. 2 and FIG. 3, and state B shown in FIG. 4, FIG. 5 and FIG. 6. In state A, the short channel 61*h* is in fluid communication with the pipeline 66 and the pipeline 67, and the specimen retention channel 62 is in fluid communication with a pipeline 56 and a pipeline 55.

On the other hand, in state B, the specimen retention channel 62 is in fluid communication with the pipeline 66 and the pipeline 67. In state B, the short channel 61*h* is not in fluid communication with any of the pipelines 55, 56, 66 and 67.

The pipeline 56 is in fluid communication with a three-way valve 16. The three-way valve 16 is in fluid communication with one end 54A of the tube pump 54. The pipeline 55 is in fluid communication with the sample suction nozzle 51. An other end 54B of the tube pump 54 is in fluid communication with the waste liquid tank 18, via a pipeline 59.

When the specimen valve 61 is not letting the specimen flow into the column 60, as shown in FIG. 2, the specimen valve 61 is in state A and the short channel 61*h* is in fluid communication with the pipeline 66 and the pipeline 67. The specimen retention channel 62 is disconnected from the feeding channel in state A. Thus, the feeding channel constitutes a first channel, which is not in fluid communication with the specimen retention channel 62.

A distal end of the sample suction nozzle 51 may be disposed inside a specimen in the dilution tank 52, and the specimen may be sucked up from the dilution tank 52 and retained in the specimen retention channel 62 by driving of the tube pump 54. In particular, because the tube pump 54 is used, the sample may be sucked up quickly.

The eluent switching unit 4 is equipped with the first switching valve 41 and the second switching valve 43.

The first switching valve 41 includes a valve body 41A. The valve body 41A includes a short channel 41*h* and a first retention channel 42. The channel length of the first retention channel 42 is longer than the channel length of the short channel 41*h*.

By turning, the valve body 41A can assume two states: state A shown in FIG. 2, FIG. 3, FIG. 4 and FIG. 5, and state B shown in FIG. 6. In state A, the short channel 41*h* is in fluid communication with the pipeline 65 and, via a three-way valve 17, a pipeline 14A or the pipeline 64. In state A, the first retention channel 42 is in fluid communication with a pipeline 14B and a pipeline 15B.

On the other hand, in state B, the first retention channel 42 is in fluid communication, via the three-way valve 17, with the pipeline 14A or pipeline 64 and with the pipeline 65. In state B, the short channel 41*h* is not in fluid communication with any of the pipelines 14A, 65, 14B and 15B.

The pipeline 14A is in fluid communication, via the three-way valve 17, with the eluent pack 12A and the main pump 63. The pipeline 14B is in fluid communication with the eluent pack 12B. An operation to suck the eluent A in the eluent pack 12A into the cylinder 63B of the main pump 63 (see arrows F1 in FIG. 3) and an operation to feed the eluent A in the cylinder 63B to the first switching valve 41 (see arrow F4 in FIG. 2) can be switched between by switching of the three-way valve 17.

The pipeline 15B is in fluid communication, via a branching portion 15D and the three-way valve 16, with the one end 54A of the tube pump 54.

When eluent B is not flowing to the column 60, the first switching valve 41 is in state A as shown in FIG. 2, and the short channel 41*h* is in fluid communication with the pipeline 14A and the pipeline 65. In state A, the first retention channel 42 is disconnected from the feeding channel. Thus, the feeding channel constitutes the first channel, which is not in fluid communication with the first retention channel 42.

When the tube pump 54 is driven in the state shown in FIG. 2, eluent B may be sucked from the eluent pack 12B and retained in the first retention channel 42. In particular, because the tube pump 54 is used, the eluent B may be sucked quickly.

The second switching valve 43 includes a valve body 43A. The valve body 43A includes a short channel 43*h* and a second retention channel 44. The channel length of the second retention channel 44 is longer than the channel length of the short channel 43*h*.

By turning, the valve body 43A can assume two states: state A shown in FIG. 2, FIG. 3 and FIG. 4, and state B shown in FIG. 5 and FIG. 6. In state A, the short channel 43*h* is in fluid communication with the pipeline 65 and the pipeline 66, and the second retention channel 44 is in fluid communication with a pipeline 14C and a pipeline 15C.

On the other hand, in state B, the second retention channel 44 is in fluid communication with the pipeline 65 and the pipeline 66. In state B, the short channel 43*h* is not in fluid communication with any of the pipelines 65, 66, 14C and 15C.

The pipeline 14C is in fluid communication with the eluent pack 12C. The pipeline 15C is in fluid communication, via the three-way valve 16, with the one end 54A of the tube pump 54.

When eluent C is not flowing to the column 60, the second switching valve 43 is in state A as shown in FIG. 2, and the short channel 43*h* is in fluid communication with the pipeline 65 and the pipeline 66. In state A, the second retention channel 44 is disconnected from the feeding channel. Thus, the feeding channel constitutes the first channel, which is not in fluid communication with the second retention channel 44.

When the tube pump 54 is driven in the state shown in FIG. 2, eluent C may be sucked from the eluent pack 12C and retained in the second retention channel 44. In particular, because the tube pump 54 is used, the eluent C may be sucked quickly.

When eluent A is to be sucked from the eluent pack 12A into the interior of the cylinder 63B of the main pump 63, as shown in FIG. 3, the eluent pack 12A end of the pipeline 14A and the pipeline 64 are put into fluid communication by the three-way valve 17. Eluent A is sucked from the eluent pack 12A into the interior of the cylinder 63B by the plunger 63A being pulled. Further, the eluent A may be discharged toward the column 60 by the first switching valve 41 end of the pipeline 14A and the pipeline 64 being put into fluid communication by the three-way valve 17, and the plunger 63A being pushed in.

When the specimen is to flow to the column 60, as shown in FIG. 4, the valve body 61A of the specimen valve 61 is put into state A thereof. The pipeline 66 and the pipeline 67 are in fluid communication with the specimen retention channel 62, and the feeding channel constitutes a fourth channel.

When eluent C is to flow to the column 60, as shown in FIG. 5, the valve body 43A of the second switching valve 43 is put into state B thereof. The pipeline 65 and the pipeline 66 are in fluid communication with the second retention channel 44. Thus, the feeding channel constitutes a third channel. Hence, the eluent C in the second retention channel 44 may be pumped to the column 60 by discharging of the main pump 63.

When eluent B is to flow to the column 60, as shown in FIG. 6, the valve body 41A of the first switching valve 41 is put into state B thereof. The pipeline 64 and the pipeline 65 are in fluid communication with the first retention channel 42. Thus, the feeding channel constitutes a second channel.

Hence, the eluent B in the first retention channel 42 may be pumped to the column 60 by discharging of the main pump 63.

The washing fluid bottle 12D accommodating the dilution and washing fluid D is placed in the liquid chromatography device 1. The specimen preparation unit 5 also functions as the liquid dilution device 70. The liquid dilution device 70 includes a washing tank 53, the dilution tank 52, a supply device 72 and a drainage device 82.

The supply device 72 includes a supply tube pump 74, a supply switching valve 76 and a supply pipeline 78.

In the specimen preparation unit 5, a supply channel of the washing and dilution fluid D may be switched by the supply switching valve 76 between the washing tank 53 side and the dilution tank 52 side thereof. Thus, the washing and dilution fluid D may be selectively supplied to one or other of the washing tank 53 and the dilution tank 52 by (forward) driving of the supply tube pump 74 in a state in which the washing and dilution fluid D supply channel has been switched.

The drainage device 82 includes a supply tube pump 84, a supply switching valve 86 and a supply pipeline 88.

A drainage channel for liquid in the washing tank 53 or the dilution tank 52 may be switched to the washing tank 53 side or the dilution tank 52 side by the supply switching valve 86. Thus, liquid may be selectively drained from one or other of the washing tank 53 and the dilution tank 52 and sent to the waste liquid tank 18 by (forward) driving of the supply tube pump 84 in a state in which the liquid drainage channel has been switched.

Figure 7:
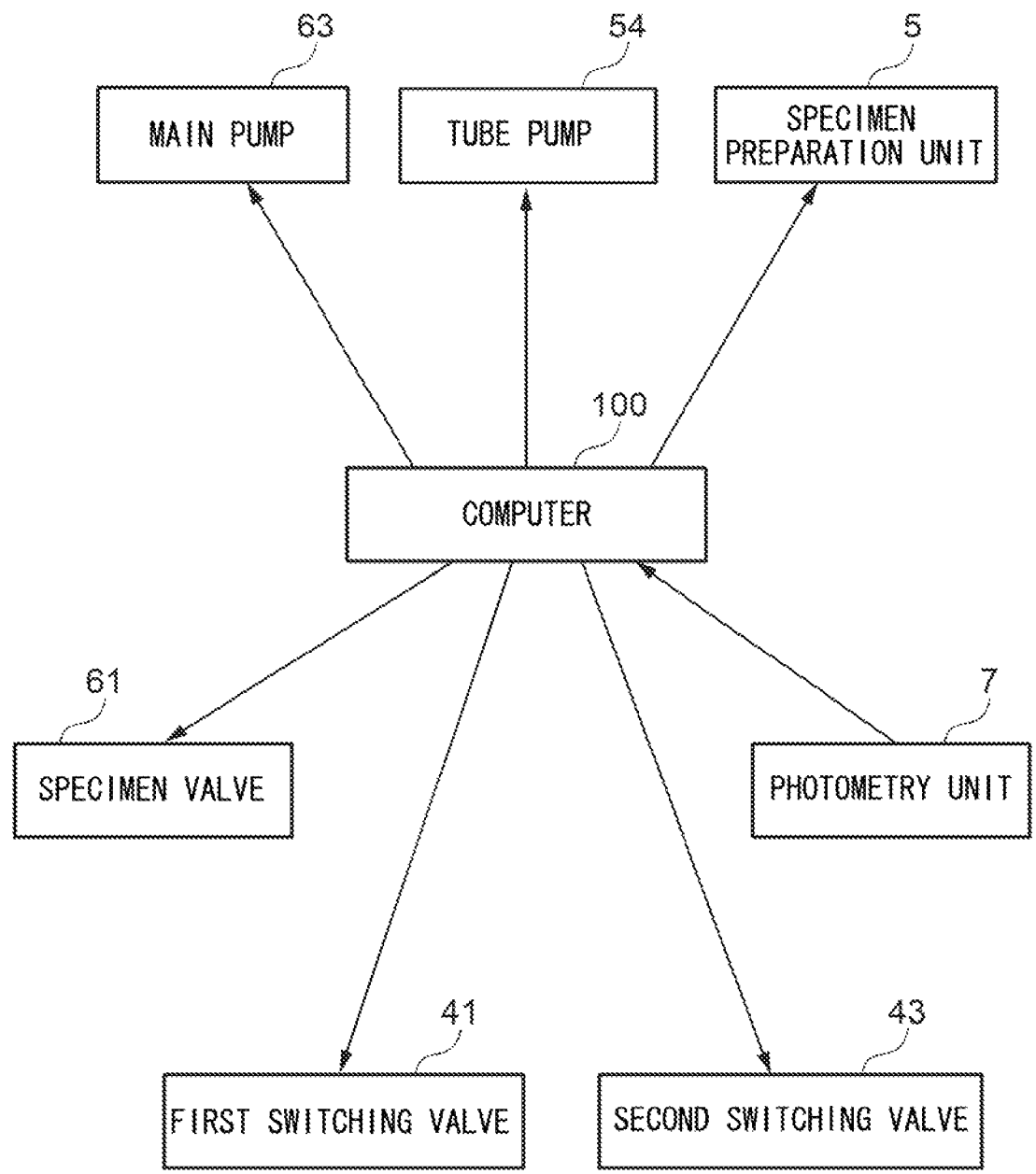
FIG. 7 is a block diagram showing relationships, in the liquid chromatography device in accordance with the exemplary embodiment, between the main pump, an auxiliary feeding pump, a specimen preparation unit, the specimen valve, the first switching valve, the second switching valve, a photometry unit, and a computer that controls all of these.

As shown in FIG. 7, in the liquid chromatography device 1 according to the present exemplary embodiment, the main pump 63, the tube pump 54, the specimen valve 61, the first switching valve 41, the second switching valve 43 and the specimen preparation unit 5 are controlled by a computer 100. Measurement results from the photometry unit 7 are inputted to the computer 100.

—Operation—

Herebelow, operation of the liquid chromatography device 1 according to the present exemplary embodiment is described.

Figure 8:
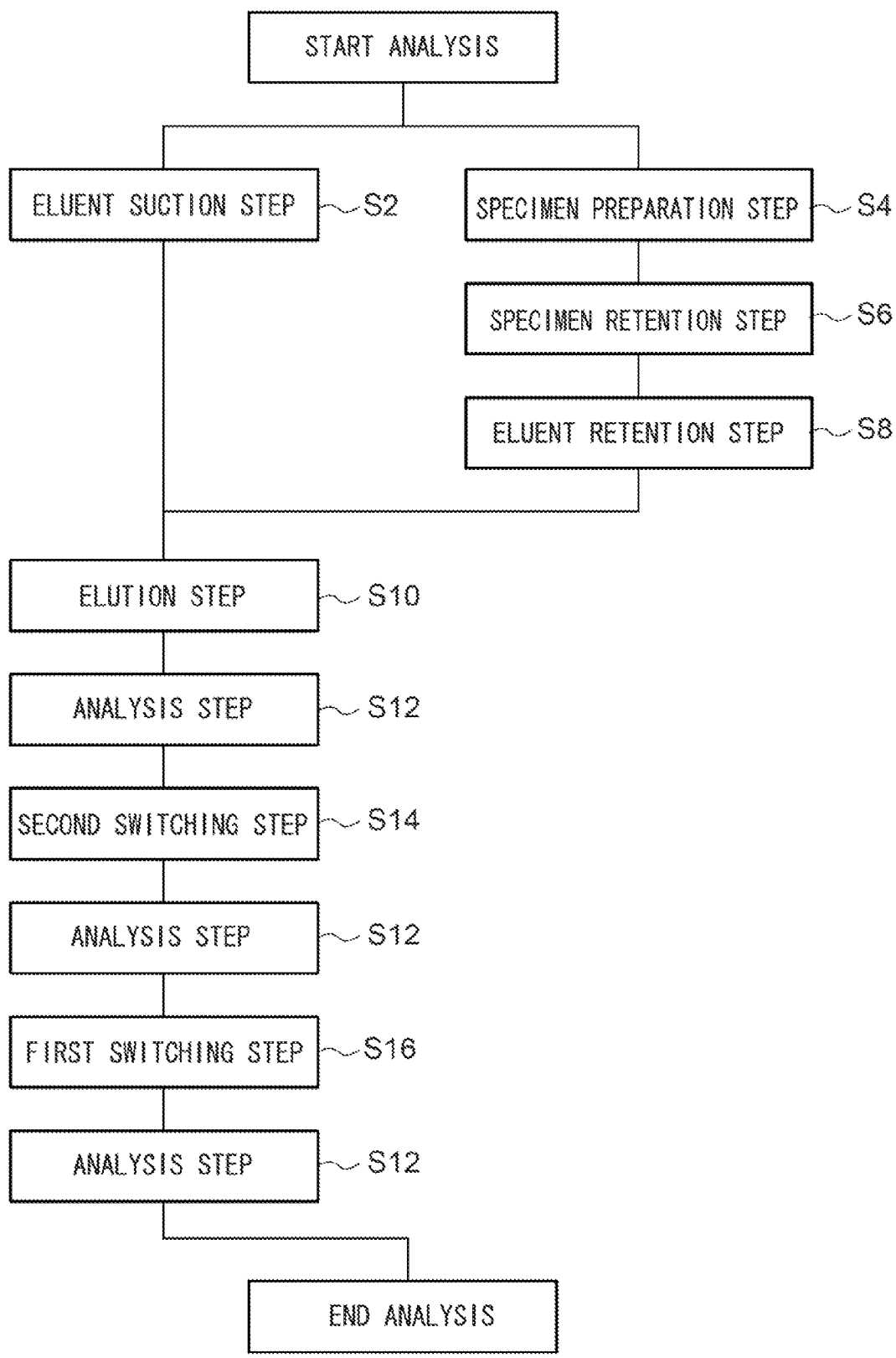
FIG. 8 is a flowchart showing operation of the liquid chromatography device in accordance with the exemplary embodiment.

As shown in FIG. 8, when a measurement is started, an eluent suction step S2 is performed. First, the eluent pack 12A end of the pipeline 14A is put into fluid communication with the main pump 63 by the three-way valve 17. Then the plunger 63A of the main pump 63 is pulled down from the cylinder 63B. As a result, a quantity of eluent A that is sufficient for carrying out the sequence of analysis operations constituted by the measurement start process, fractionation of the specimen, measurement processing, washing of the column 60, and the post-measurement process is sucked from the eluent pack 12A to the interior of the cylinder 63B.

Next, each of the first switching valve 41, the second switching valve 43 and the specimen valve 61 is put into state A thereof. Thus, the feeding channel is constituted to reach from the pipeline 64, through the first switching valve 41 end of the pipeline 14A, the pipeline 65 and the pipeline 66, to the pipeline 67. In this state, all of the first retention channel 42, the second retention channel 44 and the specimen retention channel 62 are disconnected from the feeding channel.

At the same time, a specimen preparation step S4 is performed at the specimen preparation unit 5. That is, the blood sample 13 is diluted with the washing and dilution fluid D in the dilution tank 52 to prepare the specimen.

When the specimen has been prepared, a specimen retention step S6 is performed. The distal end of the sample suction nozzle 51 is disposed within the specimen in the dilution tank 52. Then the three-way valve 16 is switched to the pipeline 56 side thereof and the tube pump 54 is driven. Liquid in the pipeline 55, the specimen retention channel 62 and the pipeline 56 is sucked by the tube pump 54. As a result, the specimen in the dilution tank 52 is charged into the specimen retention channel 62. Because the tube pump 54 is being used at this time, the liquid may be sucked quickly.

Next, an eluent retention step S8 is performed. The three-way valve 16 is switched to the pipelines 15B and 15C side thereof and the tube pump 54 is driven. As indicated by arrow F2 in FIG. 2, liquid in the pipeline 14B, the first retention channel 42 and the pipeline 15B is sucked by the tube pump 54, and eluent B is charged into the first retention channel 42.

Meanwhile, as indicated by arrow F3 in FIG. 2, liquid in the pipeline 14C, the second retention channel 44 and the pipeline 15C is sucked by the tube pump 54, and eluent C is charged into the second retention channel 44.

Because the tube pump 54 is used in the specimen retention step S6 and the eluent retention step S8, the liquids may be sucked quickly.

When the specimen, eluent B and eluent C have been charged into, respectively, the specimen retention channel 62, the first retention channel 42 and the second retention channel 44, the plunger 63A of the main pump 63 is pushed into the cylinder 63B at a constant speed, starting feeding of the eluent A, as indicated by arrow F4 in FIG. 2. The eluent A fed from the main pump 63 passes through the pipeline 64, the pipeline 65, the pipeline 66 and the pipeline 67 and is fed to the column 60. Thus, the column 60 is equilibrated.

When the column 60 has been equilibrated, an elution step S10 is performed by the following procedure.

First, as shown in FIG. 4, the specimen valve 61 is put into state B thereof and the feeding channel is switched from the first channel to the fourth channel. The liquid retained inside the specimen retention channel 62 is pushed to the pipeline 67 by the eluent A that has passed through the pipeline 66, and is fed to the column 60. In the present exemplary embodiment, the internal diameters of the pipeline 66, the specimen retention channel 62 and the pipeline 67 are narrow enough to prevent mixing of the plural kinds of liquid with one another. Therefore, mixing of the liquids in the pipeline 66, the specimen retention channel 62 and the pipeline 67 is suppressed. In the column 60, analysis components in the specimen are adsorbed.

After the specimen that was retained in the specimen retention channel 62 has been pushed out to the column 60, the eluent A is fed through the specimen retention channel 62 to the column 60. As a result, an analysis component that has been adsorbed at the column 60 is eluted by eluent A. Then, an analysis step S12 is performed and the analysis component eluted by eluent A is detected at the photometry unit 7.

When the elution of the analysis component by eluent A has ended, a second switching step S14 is performed. That is, as shown in FIG. 5, the second switching valve 43 is put into state B thereof and the feeding channel is switched from the fourth channel to the communicating third channel. The eluent C that was retained in the second retention channel 44 is fed through the pipeline 66, the specimen retention channel 62 and the pipeline 67 to the column 60. In the present exemplary embodiment, because the internal diameter of the pipeline 66 is narrow enough for the plural types of liquid to pass through without mixing with one another, mixing of the liquids in the pipeline 66, the specimen retention channel 62 and the pipeline 67 is suppressed.

When the eluent C is fed to the column 60, an analysis component adsorbed at the column 60, which has not been eluted by eluent A, is eluted by the eluent C, and is detected at the photometry unit 7.

When the elution of the analysis component by the eluent C has ended, a first switching step S16 is performed. As shown in FIG. 6, the first switching valve 41 is put into state B thereof and the feeding channel is switched from the third channel to the second channel. The eluent B that was retained in the first retention channel 42 is fed through the pipeline 65, the pipeline 66, the specimen retention channel 62 and the pipeline 67 to the column 60. The pipeline 65 also has an internal diameter narrow enough for the plural types of liquid to pass through without mixing with one another. Thus, mixing of the liquids in the pipeline 65, the pipeline 66, the specimen retention channel 62 and the pipeline 67 is suppressed.

When the eluent B is fed to the column 60, an analysis component adsorbed at the column 60, which has not been eluted by eluent A or eluent C, is eluted by the eluent B and is detected at the photometry unit 7. In a case in which the analysis components eluted by eluent C and eluent B are not targets of measurement, the column 60 can be washed by the elutions by eluent C and eluent B.

When the elution of the analysis component by the eluent B has ended, feeding of eluent A continues with the specimen valve 61, the first switching valve 41 and the second switching valve 43 being maintained in the states B thereof as shown in FIG. 6. In this manner, the post-measurement process (post-washing equilibration of the column 60) is carried out.

—Liquid Chromatography Analysis Program—

A liquid chromatography analysis program is installed in the computer 100. The liquid chromatography analysis program is for causing the computer 100 to execute processing including the eluent suction step S2, the specimen preparation step S4, the specimen retention step S6, the eluent retention step S8, the elution step S10, the analysis steps S12, the second switching step S14 and the first switching step S16.

The eluent retention step S8 encompasses a first retention step for charging the first retention channel 42 with eluent B and a second retention step for charging the second retention channel 44 with eluent C. In the liquid chromatography analysis program, either of the first retention step and the second retention step may be performed first.

The liquid chromatography analysis program installed at the computer 100 may be a program that is made simpler than the liquid chromatography analysis program described above.

The liquid chromatography analysis program may be a program from which the specimen preparation step S4 and the specimen retention step S6 are omitted.

The liquid chromatography analysis program may also be a program that causes the computer 100 to execute processing including the elution step S10 and the analysis step S12.

The computer 100 includes a control section. This control section may be structured with a CPU that controls the device as a whole, a ROM that memorizes the program and the like, a RAM that temporarily stores measurement results, and an input/output port. The computer 100 with this structure may control the liquid chromatography device 1 in accordance with commands inputted through, for example, control buttons, a keyboard or the like.

As is described hereinabove, the liquid chromatography device 1 according to the present exemplary embodiment may, with a simple structure, quickly and easily perform parallel processing of plural liquids divided between a high-pressure channel and low-pressure channels.

—Alternative Embodiments—

In the foregoing, a specific exemplary embodiment of the present invention has been described in detail, but the present invention is not to be limited to the above exemplary embodiment and numerous alternative embodiments may be embodied within the technical scope of the invention. For example, the first switching valve 41, the second switching valve 43 and the specimen valve 61 may be formed as spectacle valves at which atmosphere release ports are formed. Processing to release bubbles from a liquid channel to the atmosphere (bubble elimination processing) may be carried out by using an atmosphere release port to open the liquid channel to the atmosphere and driving the main pump 63 and the tube pump 54 as appropriate. Another process may be operated in parallel with the bubble elimination processing by driving of the tube pump 54. Thus, parallel processing of plural liquids divided between a high-pressure channel and a low-pressure channel may be performed quickly and easily with a simple structure.

The main pump 63 may also operate as a bubble elimination device. For bubble elimination processing in this structure, first, air is introduced into the main pump 63 through an atmosphere release port of the first switching valve 41 and an air layer is formed. This air layer is moved in a liquid channel, bubbles in the liquid channel are taken up into the air layer, and the bubbles are ejected together with the air layer. In this case, the introduction of bubbles by driving of the main pump 63 and subsequent ventilation processing may be conducted in parallel with another process based on driving of the tube pump 54. Thus, parallel processing of plural liquids divided between a high-pressure channel and a low-pressure channel may be performed quickly and easily with a simple structure.

According to this exemplary embodiment, while this bubble elimination processing is being implemented, for example, the operation of charging the eluent from the eluent pack 12B into the first retention channel 42 may be performed in parallel therewith.

Various devices that are capable of introducing gas may be used as a device that introduces a gas from the exterior to the main pump 63. Beside an atmosphere release port or an atmosphere release valve, this gas introduction device may be, for example, a device capable of directly introducing air into the main pump 63 using any of various kinds of switching valve.

Depending on the compositions of eluent B and eluent C in the embodiments described above, a configuration is possible in which the second switching valve 43 is switched and eluent C is fed to the column 60 after the first switching valve 41 has been switched and eluent B has been fed to the column 60. Further, in light of the fundamentals of chromatographic measurement, in the sequence of analysis operations performed in the liquid chromatography device 1, it may not be possible to clearly distinguish between a particular process included in the sequence of analysis operations and a preceding or succeeding process. For example, when a liquid that is used for the last measurement process is the same as a liquid that is used for washing of the column 60, a point in time at which the measurement process finishes cannot be identified. Similar situations may apply to other processing phases. Therefore, the present exemplary embodiment is not limited to the analysis operation states described above.

In the exemplary embodiment described above, the specimen preparation unit 5, the photometry unit 7 and the separation and adsorption unit 6 are accommodated inside the single casing 3. However, one or a number of these units may be structured as a separate body from the other units and a system linking the units may be configured.

In the exemplary embodiment described above, the tube pump 54 is used as the auxiliary feeding device, but auxiliary feeding devices are not limited to the tube pump 54.

According to the technology of the present application, parallel processing of plural liquids divided between a high-pressure channel and a low-pressure channel may be performed quickly and easily with a simple structure.

All references, patent applications and technical specifications cited in the present specification are incorporated by reference into the present specification to the same extent as if the individual references, patent applications and technical specifications were specifically and individually recited as being incorporated by reference.

What is claimed is:

1. A liquid chromatography device comprising:
    an adsorption portion that adsorbs one or more analysis components in a specimen;
    an analysis device that analyzes an analysis component eluted by an eluent;
    a main feeding device that feeds a first eluent to the adsorption portion, the first eluent eluting an analysis component;
    a feeding channel in fluid communication with the main feeding device and the adsorption portion;
    a first retention channel that retains a second eluent, the second eluent differing from the first eluent;
    an auxiliary feeding device that feeds the second eluent to the first retention channel; and
    a first switching device that switches the feeding channel to either a first channel or a second channel, the first channel allowing the first eluent to flow from the main feeding device to the adsorption portion, and the second channel allowing the second eluent to flow from the first retention channel to the adsorption portion,
    wherein the main feeding device serves as a high pressure pump, and
    wherein the auxiliary feeding device serves as a low pressure pump.

2. The liquid chromatography device according to claim 1, further comprising:
    a second retention channel that retains a third eluent, the third eluent differing from the first and second eluents;
    an auxiliary feeding device that feeds the third eluent to the second retention channel; and
    a second switching device that switches the feeding channel to either the first channel or a third channel, the third channel allowing the third eluent to flow from the second retention channel to the adsorption portion.

3. The liquid chromatography device according to claim 2, further comprising:
    a specimen retention channel that retains the specimen;
    an auxiliary feeding device that feeds the specimen to the specimen retention channel; and
    a third switching device that switches the feeding channel to either the first channel or a fourth channel, the fourth channel allowing the specimen to flow from the specimen retention channel to the adsorption portion.

4. The liquid chromatography device according to claim 3, wherein the auxiliary feeding device that feeds the specimen is the same device as at least one of the auxiliary feeding device that feeds the second eluent or the auxiliary feeding device that feeds the third eluent.

5. The liquid chromatography device according to claim 2, wherein the auxiliary feeding device that feeds the second eluent and the auxiliary feeding device that feeds the third eluent are the same device.

6. The liquid chromatography device according to claim 1, wherein the first switching device enables parallel operation of a bubble elimination process and another process, the processes using the main feeding device and the auxiliary feeding device.

7. The liquid chromatography device according to claim 1, further comprising a liquid dilution device that dilutes the specimen containing the one or more analysis components,
    wherein the adsorption portion adsorbs the one or more analysis components in the specimen that has been diluted by the liquid dilution device.

8. A liquid chromatography analysis process comprising:
    an elution step of, at a main feeding device serving as a high pressure pump, feeding a first eluent that elutes an analysis component through a feeding channel to an adsorption portion that has adsorbed one or more analysis components in a specimen and eluting the analysis component;
    an analysis step of, at an analysis device, analyzing the analysis component eluted in the elution step;
    a first retention step of, at an auxiliary feeding device serving as a low pressure pump, feeding a second eluent to and retaining the second eluent at a first retention channel, the second eluent differing from the first eluent; and
    a first switching step of switching the feeding channel to either a first channel or a second channel, the first channel allowing the first eluent to flow from the main feeding device to the adsorption portion, and the second channel allowing the first eluent to flow through the first retention channel at which the second eluent has been retained to the adsorption portion.

9. The liquid chromatography analysis process according to claim 8, further comprising a step of causing the main feeding device to function as a bubble elimination device.

10. The liquid chromatography analysis process according to claim 8, further comprising:
    a second retention step of, at an auxiliary feeding device, feeding a third eluent to and retaining the third eluent at a second retention channel, the third eluent differing from the first and second eluents; and
    a second switching step of switching the feeding channel to either the first channel or a third channel, the third channel allowing the first eluent to flow through the second retention channel at which the third eluent has been retained by the second retention step to the adsorption portion.

11. The liquid chromatography analysis process according to claim 10, further comprising a specimen retention step of, at an auxiliary feeding device, feeding the specimen to and retaining the specimen at a specimen retention channel,
    wherein the elution step includes a specimen introduction step of switching the feeding channel from the first channel to a fourth channel, the fourth channel allowing the first eluent to flow through the specimen retention channel at which the specimen has been retained by the specimen retention step to the adsorption portion.

12. A non-transitory computer-readable medium storing a liquid chromatography analysis program causing a computer to actuate a liquid chromatography device that includes:
    an adsorption portion that adsorbs one or more analysis components in a specimen;

an analysis device that analyzes an analysis component eluted by an eluent;

a main feeding device serving as a high pressure pump that feeds a first eluent to the adsorption portion, the first eluent eluting an analysis component;

a feeding channel in fluid communication with the main feeding device and the adsorption portion;

a first retention channel that retains a second eluent, the second eluent differing from the first eluent;

an auxiliary feeding device serving as a low pressure pump that feeds the second eluent to the first retention channel;

a first switching device that switches the feeding channel to either a first channel or a second channel, the first channel allowing the first eluent to flow from the main feeding device to the adsorption portion, and the second channel allowing the second eluent to flow from the first retention channel to the adsorption portion; and a computer that controls the main feeding device, the analysis device, the auxiliary feeding device and the first switching device, to execute a process comprising:

an elution step of, at the main feeding device, feeding the first eluent to the adsorption portion and eluting the analysis component;

an analysis step of, at the analysis device, analyzing the analysis component eluted in the elution step;

a first retention step of, at the auxiliary feeding device, feeding the second eluent to and retaining the second eluent at the first retention channel; and a first switching step of, with the first switching device, switching the feeding channel from the first channel to the second channel.

13. The non-transitory computer-readable recording medium according to claim 12, wherein the process further comprises:

a second retention step of, at an auxiliary feeding device, feeding a third eluent to and retaining the third eluent at a second retention channel, the third eluent differing from the first and second eluents; and a second switching step of switching the feeding channel to either the first channel or a third channel, the third channel allowing the first eluent to flow through the second retention channel at which the third eluent has been retained by the second retention step to the adsorption portion.

14. The non-transitory computer-readable recording medium according to claim 13, wherein:

the process further comprises a specimen retention step of, at an auxiliary feeding device, feeding the specimen to and retaining the specimen at a specimen retention channel; and the elution step includes a specimen introduction step of switching the feeding channel from the first channel to a fourth channel, the fourth channel allowing the first eluent to flow through the specimen retention channel at which the specimen has been retained by the specimen retention step to the adsorption portion.

* * * * *